(12) United States Patent
Micoine et al.

(10) Patent No.: US 9,637,436 B2
(45) Date of Patent: May 2, 2017

(54) CATALYST SYSTEM FOR PRODUCING KETONES FROM EPOXIDES

(71) Applicants: Kévin Micoine, Herten (DE); Ralf Meier, Dortmund (DE); Jürgen Herwig, Hünxe (DE); Angélique Bétard, Herten (DE); Thomas Quandt, Marl (DE)

(72) Inventors: Kévin Micoine, Herten (DE); Ralf Meier, Dortmund (DE); Jürgen Herwig, Hünxe (DE); Angélique Bétard, Herten (DE); Thomas Quandt, Marl (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/873,827

(22) Filed: Oct. 2, 2015

(65) Prior Publication Data
US 2016/0096794 A1    Apr. 7, 2016

(30) Foreign Application Priority Data

Oct. 2, 2014    (EP) .................................... 14187482

(51) Int. Cl.
*B01J 21/12* (2006.01)
*B01J 23/42* (2006.01)
*B01J 37/12* (2006.01)
*C07C 45/58* (2006.01)
*B01J 35/00* (2006.01)
*B01J 21/06* (2006.01)
*B01J 21/08* (2006.01)
*B01J 23/38* (2006.01)
*B01J 23/40* (2006.01)
*B01J 23/44* (2006.01)
*B01J 35/10* (2006.01)
*B01J 37/00* (2006.01)
*B01J 37/02* (2006.01)
*B01J 35/02* (2006.01)
*B01J 37/08* (2006.01)
*C07D 225/02* (2006.01)

(52) U.S. Cl.
CPC ............ *C07C 45/58* (2013.01); *B01J 21/066* (2013.01); *B01J 21/08* (2013.01); *B01J 23/38* (2013.01); *B01J 23/40* (2013.01); *B01J 23/44* (2013.01); *B01J 35/0006* (2013.01); *B01J 35/023* (2013.01); *B01J 35/1009* (2013.01); *B01J 35/1014* (2013.01); *B01J 35/1019* (2013.01); *B01J 35/1085* (2013.01); *B01J 37/0009* (2013.01); *B01J 37/0201* (2013.01); *B01J 37/0207* (2013.01); *B01J 37/08* (2013.01); *C07D 225/02* (2013.01); *C07C 2101/20* (2013.01)

(58) Field of Classification Search
CPC . B01J 21/066; B01J 21/08; B01J 21/12; B01J 23/40; B01J 23/42; B01J 23/44; B01J 23/46; B01J 23/462; B01J 23/464; B01J 23/466; B01J 23/468; B01J 35/0006; B01J 35/1014; B01J 35/1009; B01J 35/1019; B01J 35/1085; B01J 35/023; B01J 37/08; B01J 37/088; B01J 37/0009; B01J 37/0201; B01J 37/12; C07C 45/58; C07C 47/33; C07D 225/02
USPC ....... 502/242, 261–262, 300, 325, 339, 349; 540/1; 568/341
See application file for complete search history.

(56) References Cited

U.S. PATENT DOCUMENTS

| | | |
|---|---|---|
| 5,422,327 A | 6/1995 | Soled et al. |
| 5,648,589 A | 7/1997 | Soled et al. |
| 6,228,800 B1 * | 5/2001 | Yamaguchi ............... B01J 23/44 502/232 |
| 6,335,472 B1 | 1/2002 | Matsuzaki et al. |
| 6,670,303 B1 | 12/2003 | Heineke et al. |
| 9,000,223 B2 | 4/2015 | Micoine et al. |
| 2003/0139596 A1 * | 7/2003 | Kuroda ................ C07D 201/06 540/464 |
| 2003/0187283 A1 * | 10/2003 | Jansen ...................... B01J 23/56 549/523 |
| 2004/0242925 A1 | 12/2004 | Berndt et al. |
| 2006/0046929 A1 | 3/2006 | Hofstadt et al. |
| 2009/0318733 A1 * | 12/2009 | Pinkos ..................... C07C 45/34 568/366 |
| 2009/0326276 A1 * | 12/2009 | Teles ....................... C07C 45/28 568/365 |
| 2010/0191018 A1 * | 7/2010 | Teles ....................... C07C 45/28 568/363 |
| 2012/0291420 A1 | 11/2012 | Kim et al. |
| 2014/0249331 A1 | 9/2014 | Micoine et al. |

FOREIGN PATENT DOCUMENTS

EP    1 074 301 A1    2/2001
EP    1 329 448 A1    7/2003
(Continued)

OTHER PUBLICATIONS

"Studies on the catalytic oxidation of epoxides to a-diketones by Bi(0)/O2 in DMSO," Sylvain Antoniotti et al. Journal of Molecular Catalysis A: Chemical 208 (2004), pp. 135-145.*

(Continued)

*Primary Examiner* — Patricia L Hailey
(74) *Attorney, Agent, or Firm* — Oblon, McClelland, Maier & Neustadt, L.L.P.

(57) ABSTRACT

A catalyst composition is useful for producing a ketone from a compound containing at least one epoxide group, and the catalyst composition contains at least one precious metal; and at least one mixed oxide; wherein the mixed oxide contains zirconium dioxide and silicon dioxide; wherein the precious metal is supported and the support is not entirely made of the mixed oxide; and wherein a mass ratio of zirconium dioxide to silicon dioxide in the mixed oxide is 86:14 to 99.9:0.1.

17 Claims, No Drawings

(56) References Cited

FOREIGN PATENT DOCUMENTS

| EP | 1 018 498 B1 | 9/2003 |
|----|---|---|
| EP | 2 772 478 A1 | 9/2014 |
| JP | 2000-191565 A | 7/2000 |
| JP | 2005-528976 A | 9/2005 |
| JP | 2011-98981 A | 5/2011 |
| JP | 2014-169289 A | 9/2014 |
| WO | WO 02/051540 A1 | 7/2002 |
| WO | WO 03/002493 A1 | 1/2003 |
| WO | WO 03/092887 A1 | 11/2003 |
| WO | WO 2007/149799 A1 | 12/2007 |

OTHER PUBLICATIONS

Singaporean Search Report issued Dec. 14, 2015 in Patent Application No. 10201508161Y.

Japanese Office Action issued Sep. 5, 2016 in Patent Application No. 2015-197050 (English translation only).

\* cited by examiner

US 9,637,436 B2

CATALYST SYSTEM FOR PRODUCING KETONES FROM EPOXIDES

BACKGROUND OF THE INVENTION

Field of the Invention

The present invention relates to a catalyst composition comprising at least one precious metal and at least one mixed oxide comprising zirconium dioxide and silicon dioxide. Furthermore, its preparation and its use are a subject-matter of the invention. Moreover, a process for producing ketones and a process for the synthesis of lactams are claimed.

Discussion of the Background

The patent application EP-A-2772478 (US 2014/0249331) describes a process for producing a ketone from an epoxide using a mixture comprising at least one precious metal and at least one metal oxide as catalyst system, where the metal oxide comprises zirconium dioxide. Using pure zirconium dioxide as metal oxide, the epoxycyclododecane was able to be converted to cyclododecanone with yields of up to more than 96%.

Although this process provides the ketone in high selectivity, considerable amounts of catalyst, long reaction times and high temperatures are required, which has an adverse cost effect on any industrial process.

SUMMARY OF THE INVENTION

The aim now was to adapt the rearrangement of epoxides to ketones in such a way that the amount of catalyst or the reaction time can be reduced. Moreover, the ketone should be obtained in at least equally high selectivity and/or yield. Moreover, it would be a processing advantage if the temperature of the reaction could turn out lower than in processes of the related art.

Catalyst compositions of the type specified at the start have now been found which are able to solve the problem.

The present invention provides a catalyst composition, comprising:
  at least one precious metal; and
  at least one mixed oxide;
  wherein the mixed oxide comprises zirconium dioxide and silicon dioxide;
  wherein the precious metal is supported and the support is not entirely made of the mixed oxide; and
  wherein a mass ratio of zirconium dioxide to silicon dioxide in the mixed oxide is 86:14 to 99.9:0.1.

In another embodiment, the present invention provides a process for producing a catalyst composition as above, comprising:
  a) preparing a mouldable mass which at least comprises
    i. a zirconium compound,
    ii. silicon dioxide as solid, and
    iii. water, and
  b) calcining the mouldable mass at a temperature of from 300 to 500° C. to prepare the mixed oxide.

The present invention also relates to a process for producing a ketone, comprising:
  reacting a compound containing at least one epoxide group in the presence of a catalyst composition;
  wherein the catalyst composition comprises at least one precious metal and at least one mixed oxide, wherein the mixed oxide comprises zirconium dioxide and silicon dioxide, wherein the precious metal is supported on a support and wherein a mass ratio of zirconium dioxide to silicon dioxide in the mixed oxide is 86:14 to 99.9:0.1, and wherein the support is the mixed oxide or the support does not consist of the mixed oxide.

Moreover, the present invention relates to a process for the synthesis of a lactam, comprising:
  producing a ketone as above and reacting said ketone to produce said lactam.

DETAILED DESCRIPTION OF THE INVENTION

All ranges mentioned below include all values and sub-values between the lower and upper limits of the ranges.

The compositions comprise at least one precious metal and at least one mixed oxide, where the mixed oxide comprises zirconium dioxide and silicon dioxide. The mass ratio of zirconium dioxide to silicon dioxide in the mixed oxide is 86:14 to 99.9:0.1, preferably 90:10 to 97:3. The stated mass ratio excludes, for example, silicon dioxide doped with zirconium dioxide. The mass ratio is calculated on the basis of the zirconium and silicon compounds used for the mixed oxide.

In a first embodiment, the precious metal is not supported (system I).

In a second embodiment, the precious metal is supported, where the support does not consist of the mixed oxide (system II). The term "does not consist of" thus in conclusion excludes a support which comprises 100% by weight mixed oxide, based on the total weight of the support. In a preferred embodiment, the support does not comprise the mixed oxide or consist of it. This preferred embodiment thus encompasses both the case that the support does not consist of the mixed oxide, and also the case that the support does not comprise the mixed oxide. The last-mentioned case includes the limiting case that the support does not consist of the mixed oxide. Impurities up to 1% by weight mixed oxide, caused for technical reasons, based on the total weight of the support, are excluded.

The support of the precious metal is preferably selected from silicon dioxide, aluminum oxide, activated carbon or mixtures thereof, with silicon dioxide being preferred. The specific surface area of the mixed oxide, measured according to BET methods, is preferably 5-155 $m^2/g$.

In a third embodiment of the invention (system III), the mixed oxide cannot be preparable from organosilicon compounds. The specific surface area of the mixed oxide, measured according to BET methods, is 5-155 $m^2/g$ and the precious metal is supported on the mixed oxide (the mixed oxide acts as a support). In this connection, the mixed oxide has a monomodal pore radius distribution. In this connection, it is preferred that the mixed oxide can be prepared from silicon dioxide which has a particle size of at least 100 nm.

The pore radius distribution can, for example, be influenced by the addition of pore formers. In this connection, the person skilled in the art can ascertain, by means of corresponding preliminary experiments, whether monomodal or higher-grade distributions are obtained.

The pore radius distribution of the mixed oxides is determined by means of mercury porosimetry. Mercury porosimetry was measured on Pascal 440 and Pascal 140 devices from CE Instruments with a maximum pressure of 4000 bar in accordance with DIN 66133.

The three embodiments of the invention comprising the systems I, II and III are referred to as catalyst systems according to the invention.

Systems II and III are preferred catalyst compositions, with system II being particularly preferred. The advantage of system II is that support and precious metal, particularly in the case of continuous processes, can be separate from the mixed oxide. As a result of this, a separate reaction implementation is made possible. Moreover, the separation of the precious metal from the mixed oxide reduces the ageing of the precious metal (the selectivity is reduced with ageing).

The mixed oxide of systems I and II preferably has a BET surface area which is in the range of 5-155 $m^2/g$.

It is preferred that the BET surface area of the mixed oxides of the catalyst systems according to the invention is in a range from 80 to 150 $m^2/g$. The BET surface area is measured in accordance with DIN 66131 and DIN ISO 9277. A BET surface area above 155 $m^2/g$ leads to a lower selectivity.

Surprisingly, the catalyst compositions according to the invention catalyze the formation of the ketones during the rearrangement of epoxide compounds. The ketone can be obtained in high yield and purity. Furthermore, it is possible to use smaller catalyst amounts compared to the related art and/or realize shorter reaction times. Moreover, the reactions are catalyzed at lower temperatures.

Catalyst compositions with mixed oxides outside of the specified mass ratio exhibit significantly lower activities. Moreover, the selectivity of the ketone formation decreases during the rearrangement of epoxides.

In the context of the present invention, mixed oxide is understood as meaning a composition which comprises at least zirconium dioxide and silicon dioxide. Zirconium dioxide and silicon dioxide are not present in the mixed oxide as concrete compounds, but serve merely as a base for calculating the mass ratios. The mixed oxide is obtained by calcination. The mixed oxide therefore does not constitute a physical mixture of zirconium dioxide and silicon dioxide, but a chemical mixture comprising at least silicon and zirconium cations with a unique crystal structure. In this regard, a physical mixture which comprises at least the two oxides and has not been calcined does not constitute a mixed oxide for the purposes of the invention. Nor is zirconium dioxide—doped or coated silicon dioxide included.

The mixed oxide comprises zirconium dioxide and silicon dioxide or consists of these two oxides. The fraction of the sum of zirconium dioxide and silicon dioxide in the mixed oxide is preferably at least 20% by weight and preferably at least 30% by weight, particularly preferably 50% by weight and very particularly preferably 95% by weight, in each case based on the total weight of the mixed oxide. The mixed oxide particularly preferably consists of zirconium dioxide and silicon dioxide.

The mixed oxide of the catalyst system can have an average bulk density of from 0.5 to 2 $g/cm^3$. The bulk density is measured by firstly weighing an empty 1000 ml measuring cylinder. The mixed oxide is then poured in up to the 500 ml mark. The filled cylinder is weighed again, the weight difference between the filled and empty measuring cylinder giving the bulk density of the material in $g/cm^3$.

The catalyst compositions according to the invention comprise the mixed oxide. Moreover, a support for the precious metal can be present which does not consist of the mixed oxide (inert support, system II). Preferably, the support does not comprise the mixed oxide or consist of it. The mixed oxide as support, and also the inert support, can be present as powders or as mouldings, preference being given to these supports as mouldings. It is likewise preferred that the mixed oxide is present as moulding if the mixed oxide does not function as precious metal support.

Suitable mouldings are beads, extrudates, tablets, granules and pellets. The conversion of powders to mouldings is described for example in chapter 9 "Shaping of Solid Catalysts" in the book "Synthesis of Solid Catalysts", ed K. P. de Jong, Wiley-VCH Verlag GmbH & Co. KGaA, Weinheim, Germany (2009).

The weight-based ratio of mixed oxide to precious metal for all catalyst systems can be 99.9:0.1 to 50:50, preferably 99.5:0.5 to 80:20 and preferably 99:1 to 90:10.

If the precious metal is supported (catalyst systems II and III), the fraction of precious metal, based on the total weight of precious metal and support, can be 0.01 to 5% by weight, preferably 0.05 to 2.5% by weight and preferably 0.3 to 2.0% by weight. The precious metal can be distributed on or within the support.

The precious metal of the catalyst system is preferably selected from ruthenium, rhodium, palladium, osmium, iridium, platinum and mixtures thereof, with ruthenium, palladium and platinum being preferred and ruthenium and palladium being particularly preferred and palladium being very particularly preferred. In the series of the three precious metals ruthenium, palladium and platinum, platinum is less suitable because of its comparatively low selectivity with regard to CDON. The precious metal can be present as powder (unsupported) or in supported form. The precious metals can be present as elemental metals or in the form of their oxides, preference being given to elemental metals.

The invention further provides a process for producing the catalyst composition according to the invention. The composition comprises at least one precious metal and at least one mixed oxide. To produce the mixed oxide, firstly a mouldable mass is prepared which at least comprises a zirconium compound, silicon dioxide as solid and water. The mouldable mass is then calcined at a temperature of from 300 to 500° C., preferably 400 to 500° C. To produce the system III it is necessary that the silicon dioxide has a pore size $d_{50}$ of at least 100 nm. For the system III, it is preferred that no polymers selected from polyalkylene pyrrolidones such as polyvinylpyrrolidone, polyamines, polyacrylates, polyalcohols, polysiloxanes or mixtures thereof are added. As a result of this, a bimodal pore radius distribution is prevented from arising.

A silicon dioxide as solid is understood as meaning a powder which does not form a stable dispersion in water. The silicon dioxide as solid preferably has a particle size $d_{50}$ of less than 500 μm. Preferably, the particle size is less than 500 μm, this upper limit being determined by means of sieve analysis (mesh of 500 μm; this upper limit, determined by means of sieve analysis, is consequently a maximum value and not an average value $d_{50}$). Likewise, the solid preferably has a particle size $d_{50}$ of greater than 100 nm (for systems I and II). For all systems I, II and III, the particle size $d_{50}$ is preferably greater than 500 nm and particularly preferably greater than 1 μm. The particle size $d_{50}$ will be ascertained by laser diffraction in accordance with ISO 13320:2009. For the measurement operation, solid (according to manufacturers instructions) is placed into the Scirocco 2000 dispersing unit of a Malvern Mastersizer 2000. The pressure selected is 1 bar and the measurement is carried out.

Colloidal solutions of $SiO_2$ such as Ludox (Grace Davison) and Köstrosol (CWK Bad Köstritz) are not preferred. These types of colloidal solutions generally comprise individual $SiO_2$ particles with a size $d_{50}$ between 5 and 30 nm. In order to ascertain the particle size of $SiO_2$ in a colloidal solution, a Zetasizer of the nano line from Malvern is used. The measurement is carried out at room temperature.

Preferably, the silicon dioxide is produced by means of pyrogenic methods. The process is known to the person skilled in the art, e.g. from the series of papers "Fine Particles" No. 11 (7th Edition, 2003), company journal of Degussa AG.

The zirconium compound is preferably selected from zirconium dioxide, zirconium hydroxide, zirconium acetate, zirconium nitrate, zirconium oxychloride, ammonium zirconium carbonate or mixtures thereof. Preference is given to using zirconium dioxide, zirconium hydroxide or mixtures thereof.

Zirconium hydroxide is understood as meaning zirconium (IV) hydroxide.

It is likewise preferred to select the zirconium compound from a mixture comprising A and B. In this connection, A comprises zirconium dioxide, zirconium hydroxide and mixtures thereof. B is selected from zirconium acetate, zirconium nitrate, zirconium oxychloride, ammonium zirconium carbonate and mixtures thereof. The fraction of zirconium from A is preferably at least 85 mol %, preferably at least 90 mol %, based on the sum of zirconium from A and B.

As a result of the calcination, the zirconium compounds are reacted at least partially to give zirconium dioxide. In this regard, zirconium compounds, apart from zirconium dioxide itself, are referred to as precursors.

Preferably, the person skilled in the art selects time conditions through which at least 50 mol %, preferably at least 90 mol %, particularly preferably 95 mol % and very particularly preferably 100 mol %, of the zirconium compounds, in each case based on the sum of all zirconium compounds, have reacted to give zirconium dioxide.

To produce system II, the precious metal can be impregnated on an inert support, where the support does not consist of the mixed oxide. Preferably, the support does not comprise the mixed oxide or consist of it. For this purpose, every impregnation method known to the person skilled in the art can be used, such as the application of a precious metal solution to the support.

To produce system III, the precious metal can be impregnated on the mixed oxide as support. For this purpose, every impregnation method known to the person skilled in the art can be used, such as the application of a precious metal solution to the support.

The person skilled in the art can adjust the size of the BET surface area of the mixed oxide by known measures in order to obtain, for example, surface areas of less than 155 m$^2$/g. The higher the fraction of silicon dioxide in the mixed oxide, the higher the surface area will be. Consequently, at most 14% by weight of silicon dioxide, based on the total weight of the mixed oxide, are present. Furthermore, the calcination temperature influences the surface area: The lower the set temperature, the higher the surface area will be. Consequently, the calcination temperature is not below 300° C., preferably not below 400° C. Moreover, preferably no polymers for enlarging the surface area, as is described for example in EP-A-2108631 (US 2009/0255402), are present. By means of a few experiments, the person skilled in the art is able to undertake an adjustment of the surface area by virtue of the specified parameters.

The mixed oxide can be reshaped into mouldings before or after calcination, preference being given to moulding formation prior to the calcination. The mouldable mass can comprise organic binders (e.g. polymers such as cellulose ethers, polysaccharides, polyethylene oxide), pore formers (e.g. waxes, organic polymers, preferably no organosilicon compounds), inorganic acids such as nitric acid, inorganic bases such as sodium hydroxide solution or mixtures thereof. The acids and/or bases can be used to adjust the rigidity and mouldability of the mixed oxide. Preferably excluded as pore formers for the system III are polyalkylene pyrrolidones such as polyvinylpyrrolidone, polyamines, polyacrylates, polyalcohols, polysiloxanes or mixtures thereof, which encourage the formation of a bimodal pore distribution, as described for example in EP-A-1074301. An example of such a polymer is poly(vinylpyrrolidone) (PVP).

The invention further provides the use of a catalyst composition K for producing ketones from a compound containing at least one epoxide group. The catalyst composition K comprises at least one precious metal and at least one mixed oxide, where the mixed oxide comprises zirconium dioxide and silicon dioxide and the mass ratio of zirconium dioxide to silicon dioxide in the mixed oxide is 86:14 to 99.9 to 0.1. The precious metal can be supported on the mixed oxide (system III).

Preferably, a catalyst composition according to the invention or a catalyst composition prepared in accordance with a method according to the invention is used, with system II being preferred.

The invention further provides a process for producing ketones, preferably cyclododecanone, from a compound containing at least one epoxide group, where a catalyst composition K is used. Preferably, a catalyst composition according to the invention or a catalyst composition prepared in accordance with a method according to the invention is used, with system II being preferred.

The process constitutes a heterogeneous catalysis.

The quantitative fraction of precious metal, based on the quantitative amount of the compound containing at least one epoxide group (compound E), can be 0.00001 to 0.1, preferably 0.0001 to 0.01. The quantitative fraction of mixed oxide in the catalyst system, based on the quantitative amount of compound E, can be 0.001 to 100, preferably 0.005 to 5.

The compound E can be aliphatic or cycloaliphatic, with cycloaliphatic compounds being preferred. Preferably, 4 to 20 carbon atoms, preferably 6 to 16 carbon atoms, particularly preferably 8 to 14 carbon atoms, very particularly preferably 10 to 12 carbon atoms and in particular 12 carbon atoms are comprised.

The compound E can contain one or more epoxide groups, with monoepoxide compounds being preferred.

Furthermore, the compound can be saturated or unsaturated. For example, one or two double bonds can be present.

Preferred compounds E are monoepoxycycloalkanes, monoepoxycycloalkanedienes and monoepoxycycloalkenes, with monoepoxycycloalkanes being particularly preferred. A very particularly preferred compound E is monoepoxycyclododecane.

It has been found that the formation of the corresponding alcohol derivative as by-product depends on the pressure of the hydrogen: As the pressure increases, so too does the alcohol fraction, meaning that the ketone selectivity decreases.

The process according to the invention can be carried out at a hydrogen pressure of from 0 up to 100 bar, with the hydrogen pressure preferably being adjusted to 0 to 5 bar and preferably to 0 to 2.5 bar. The hydrogen pressure is particularly preferably 0 to 0.9 bar, very particularly preferably 0 to 0.5 bar. The process according to the invention can be carried out without hydrogen. However, in order to suppress unsaturated by-products, it is preferred to initially introduce at least a small hydrogen fraction. This can have 0.05 to 0.5 bar, preferably 0.1 to 0.4 bar. Alternatively, a hydrogenation step can be provided following the rearrangement.

The pressure data specified above refers to the partial pressure of hydrogen in the system. Usually, components of the reaction mixture, including of the solvent, air or inert gases such as nitrogen or argon, are further gaseous constituents of the system.

As a result of the low hydrogen pressures, a considerably lower technical expenditure compared to the related art is required, especially as regards the suitable apparatus, in order to be able to work with hydrogen. The particular advantage of the invention is that the ketone can be obtained in high yields without the presence of hydrogen.

The temperature during the reaction is preferably adjusted to a range from 100 to 350° C., preferably 150 to 250° C. and particularly preferably between 180 and 230° C. The reaction can be carried out with a compound E, which is in the liquid or gaseous state.

The process according to the invention can be carried out in organic solvents, it being preferred to work without solvents and thus to use no organic solvents. Suitable solvents are, for example, alkanes such as n-hexane, n-heptane, n-tetradecane and cyclohexane; ethers such as tetrahydrofuran and dioxane; alkanols such as methanol, ethanol and t-butanol; esters such as ethyl acetate and butyl acetate. The solvents can be used on their own or in mixtures. The solvent is preferably used in an amount which is 20 times or less than, preferably 10 times or less than, the weight of compound E.

The process can be carried out continuously or discontinuously. The purification of the ketone can take place by distillation, crystallization or recrystallization.

In a preferred embodiment of the invention, monoepoxycyclododecane is converted to cyclododecanone without solvents at temperatures of 170 to 250° C., where the catalyst system used is a mixture of palladium on inert support with a palladium fraction of 0.5 to 2% by weight, based on the total weight of the support, and of a mixed oxide from the calcination of a mixture comprising at least zirconium hydroxide and silicon dioxide (system II). During the reaction, at most 0.9 bar of hydrogen, very particularly preferably at most 0.1 bar, are used.

The invention further provides a process for the synthesis of lactams (lactam process according to the invention), in which the aforementioned process according to the invention for producing ketones is used. The compound E is preferably selected from aliphatic monoepoxycycloalkanes, aliphatic monoepoxycycloalkanedienes and aliphatic monoepoxycycloalkenes, with monoepoxycycloalkanes being preferred.

If the ketone is present in a mixture with the corresponding alcohol derivative, a dehydrogenation of the alcohol to the ketone can take place. The ketone may subsequently be oximated. The Beckmann rearrangement to give the lactam may be carried out as a subsequent step using sulphuric acid or cyanuric chloride. The lactams may be subjected to further processing by polycondensation to give polyamides.

The dehydrogenation, the oximation, the Beckmann rearrangement and the condensation reaction are known to the person skilled in the art.

In a preferred embodiment of the lactam process according to the invention, laurolactam is prepared from monoepoxycyclododecane (or cyclododecane epoxide or 1,2-cyclododecane epoxide).

In the context of the preferred lactam method, monoepoxycyclododecane is obtainable by the following reaction steps: 1,3-butadiene is reacted to give cyclododecatriene by cyclotrimerization. This is followed by a hydrogenation to give the cyclododecene. The cyclododecane epoxide is obtained by subsequent epoxidation. The person skilled in the art in the field of the synthesis of organic compounds can prepare other aliphatic and cycloaliphatic compounds E analogously to the synthesis of monoepoxycyclododecane.

Even in the absence of further information it is assumed that a person skilled in the art can make very extensive use of the above description. The preferred embodiments and examples are therefore to be interpreted merely as descriptive disclosure, and certainly not as disclosure that is in any way limiting.

The present invention is explained in more detail below with reference to examples. Alternative embodiments of the present invention are obtainable analogously.

Having generally described this invention, a further understanding can be obtained by reference to certain specific examples which are provided herein for purposes of illustration only, and are not intended to be limiting unless otherwise specified.

EXAMPLES

The percentages in the case of catalysts give the weight fraction of the precious metal, based on the total weight of the catalyst comprising precious metal and support. The abbreviation "calc." stands for "calcined". The abbreviations for the substances are: CDAN: Cyclododecane; CDEN: Cyclododecene; ECD: Epoxycyclododecane; CDON: Cyclododecanone; CDENON: Cyclododecenone (isomer mixture); CDOL: Cyclododecanol; CDENOL: Cyclododecenol (isomer mixture).

The weight data for the precious metal refer, unless stated otherwise, to the total weight of the support of the precious metal.

The silicon dioxide (Aerosil) used in the examples was obtained via a pyrogenic method.

PREPARATION OF THE MIXED OXIDES

Example A (not According to the Invention)

Preparation of $ZrO_2$ mouldings

Oxide 1 (100% $ZrO_2$):

2000 g of zirconium hydroxide powder (XZO 1501/09, MEL Chemicals) were calcined to zirconium dioxide in a muffle furnace at 450° C. for 3 h. After cooling, 1000 g of zirconium dioxide powder were mixed with 10 g of cellulose ether (Tylose MH1000 P2 from SE Tylose). 520 g of water were then added, and the mixture was kneaded until an extrudable mass was obtained. The mass was processed and cut using a roller die extruder to give strands with a diameter of 1.6 mm. The green bodies were dried at 110° C. for 4 hours and then calcined at 450° C. for 2 hours.

The BET surface area of the calcined mouldings was 64 $m^2/g$. The pore radius distribution was monomodal.

The oxide 1 corresponds to the zirconium dioxide used in table 3, last entry, and table 4, fourth and fifth entry in EP-A-2772478.

Example B

Preparation of Mouldings from $ZrO_2$ and $SiO_2$ (Mixed Oxide)

Oxide 2 (95% $ZrO_2$, 5% $SiO_2$):

773 g of zirconium dioxide powder (from Example A) were mixed with 40 g of silicon dioxide (Aerosil 200 V, Evonik), and 8 g of Tylose MH1000. Then, 450 g of water were added, and the mixture was kneaded until an extrudable mass was obtained. The mass was processed and cut using a roller die extruder to give strands with a diameter of 1.6 mm. The green bodies were dried at 110° C. for 4 hours and then calcined at 450° C. for 2 hours.

The pore radius distribution was monomodal.

Oxide 3 (95% $ZrO_2$, 5% $SiO_2$):

1000 g of zirconium hydroxide (XZO 1501/09, MEL Chemicals), 40 g of Aerosil 200 V, 20 g of wax (Licowax C Micro Powder PM from Clariant) and 2 g of cellulose ether (Tylose MH1000 P2 from SE Tylose) were introduced in a mixer and dry-mixed. Then, 8.3 g of a 30% strength NaOH solution in 800 g of water were added and the mixture was kneaded until an extrudable mass was obtained. The mass was processed and cut using a roller die extruder to give strands with a diameter of 1.8 mm. The green bodies were dried at 110° C. for 4 hours and then calcined at 450° C. for 2 hours.

The calcined mouldings comprised $ZrO_2$ and $SiO_2$ in a mass ratio of 95:5. The calcined mouldings had an average diameter of 1.16 mm and a BET surface area of 150 $m^2/g$.

Further oxides (4 to 9) were prepared under analogous conditions. The following were varied: the amount of zirconium hydroxide, silicon dioxide, and also type and amount of the zirconium compounds B and inorganic acids and/or bases. As pulverulent shaping auxiliary, 20 g of Licowax and 2 g of Tylose MH1000 P2 were always added. The precise conditions are given in the table below.

In the oxides 10 and 11, ammonium zirconium carbonate (Bacote 20, oxide 10) or zirconyl nitrate (oxide 11) were used as zirconium compound B.

Example C (not According to the Invention)

Preparation of $ZrO_2$-Doped $SiO_2$

Oxide 12 (15% $ZrO_2$, 85% $SiO_2$):

85 g of $SiO_2$ support (Aerolyst® 3041, Evonik) were impregnated with 85 ml of a 5.5% by weight NaOH solution and dried at 110° C. for 4 h. In parallel to this, 40 g of $ZrOCl_2 \cdot 8H_2O$ were dissolved in water and the solution was diluted to 85 ml. The dried support was impregnated with the zirconyl chloride solution, dried overnight at 110° C. and then calcined at 450° C. for 2 hours.

Oxide 13 (15% $ZrO_2$, 85% $SiO_2$):

50 g of a 30% zirconium acetate solution ($Zr(OA_c)$) was diluted to 85 ml. 85 g of $SiO_2$ support (Aerolyst® 3041, Evonik) was impregnated with the zirconyl chloride solution, dried over night at 110° C. and then calcined at 450° C. for 2 hours.

The pore radius distributions of all of the supports in examples A to C were monomodal.

TABLE 1

Overview of the prepared mixed oxides

| Oxide | Zr Precursor | $SiO_2$ | Other | $ZrO_2:SiO_2$ (mass ratio) | BET ($m^2/g$) |
|---|---|---|---|---|---|
| 3 | 1000 g $Zr(OH)_4$ | 40 g Aerosil 200V | 8.3 g of a 30% strength NaOH solution in 800 g of $H_2O$ | 95:5 | 150 |
| 4 | 1000 g $Zr(OH)_4$ | 8 g Aerosil 200V | 65.4 g of a 65% strength $HNO_3$ solution in 530 g of $H_2O$ | 99:1 | 78 |
| 5 | 1000 g $Zr(OH)_4$ | 24 g Aerosil 200V | 66 g of a 65% strength $HNO_3$ solution in 550 g of $H_2O$ | 97:3 | 79 |
| 6 | 1000 g $Zr(OH)_4$ | 40 g Aerosil 200V | 84 g of a 65% strength $HNO_3$ solution in 541 g of $H_2O$ | 95:5 | 86 |
| 7 | 1000 g $Zr(OH)_4$ | 85.5 g Aerosil 200V | 84 g of a 65% strength $HNO_3$ solution in 565 g of $H_2O$ | 90:10 | 109 |
| 8* | 894 g $Zr(OH)_4$ | 122 g Aerosil 200V | 7.45 g of a 30% strength NaOH solution in 830 g of $H_2O$ | 85:15 | 213 |
| 9* | 1000 g $Zr(OH)_4$ | 142 g tetraethyl orthosilicate | 400 g water | 95:5 | — |
| 10 | 1000 g $Zr(OH)_4$ | 40 g Aerosil 200 V | 8.3 g of a 30% strength NaOH solution in 700 g of $H_2O$, 118 g Bacote 20 (MEL Chemicals) | 95:5 | 131 |
| 11 | 1000 g $Zr(OH)_4$ | 40 g Aerosil 200 V | 90 g of a 65% strength $HNO_3$ solution in 450 g of $H_2O$, 118 g zirconyl nitrate (MEL Chemicals) | 95:5 | 113 |
| 12* | 40 g $ZrOCl_2 \cdot 8H_2O$ | 85 g silica support | 85 ml of a 5.5% by weight NaOH solution | 15:85 | — |
| 13* | 50 g $Zr(OAc)_4$ (30% strength) | 85 g silica support | — | 15:85 | — |

*not according to the invention

CATALYST COMPOSITIONS

Example D

Composition of Mixed Oxide and Pd-Impregnated Silicon Dioxide (Catalyst System II)

2000 g of silicon dioxide mouldings (Aerolyst® 3041, Evonik) were introduced into a rotating glass drum and heated to 110° C. In parallel, 100 g of a 10% strength Pd(II) nitrate solution were weighed and diluted to 1910 g by adding water. The solution was then sprayed onto the $SiO_2$ support. A thin precious metal shell was formed. The impregnated mouldings were then calcined for 10 hours in a reducing atmosphere (0.4% by volume hydrogen in the nitrogen) at 200° C. The weight fraction of Pd with regard to the $SiO_2$ support was 0.5%. These Pd/$SiO_2$ mouldings were compounded with the various oxides 1 to 13 from Examples A, B, C.

Catalyst Compositions:
Composition 1*: Oxide 1 (50% by weight) and Pd/$SiO_2$ (50% by weight) and Pd/$SiO_2$ (50% by weight); this composition comprises the same constituents as the catalyst compositions used in table 3, last entry and table 4, fourth and fifth entry in EP-A-2772478.
Composition 2: Oxide 2 (50% by weight) and Pd/$SiO_2$ (50% by weight)
Composition 3: Oxide 3 (50% by weight) and Pd/$SiO_2$ (50% by weight)
Composition 4: Oxide 4 (50% by weight) and Pd/$SiO_2$ (50% by weight)
Composition 5: Oxide 5 (50% by weight) and Pd/$SiO_2$ (50% by weight)
Composition 6: Oxide 6 (50% by weight) and Pd/$SiO_2$ (50% by weight)
Composition 7: Oxide 7 (50% by weight) and Pd/$SiO_2$ (50% by weight)
Composition 8*: Oxide 8 (50% by weight) and Pd/$SiO_2$ (50% by weight)
Composition 9*: Oxide 9 (50% by weight) and Pd/$SiO_2$ (50% by weight)
Composition 10: Oxide 10 (23% by weight) and Pd/$SiO_2$ (77% by weight)
Composition 11: Oxide 11 (23% by weight) and Pd/$SiO_2$ (77% by weight)
Composition 12: Oxide 3 (9% by weight) and Pd/$SiO_2$ (91% by weight)
Composition 13: Oxide 3 (23% by weight) and Pd/$SiO_2$ (77% by weight)
Composition 14: Oxide 3 (33% by weight) and Pd/$SiO_2$ (67% by weight)
Composition 15: Oxide 6 (20% by weight) and Pd/$SiO_2$ (80% by weight)
Composition 16*: $TiO_2$—$SiO_2$ mixture (calcined) VP TiO2 545 S from pyrogenic process of Evonik Industries (9% by weight) and Pd/$SiO_2$ (91% by weight)
Composition 17*: $TiO_2$—$SiO_2$ mixture (calcined) VP TiO2 590 S from pyrogenic process of Evonik Industries (9% by weight) and Pd/$SiO_2$ (91% by weight)
Composition 18*: $SiO_2$ Aerosil® 200V (50% by weight) and Pd/$SiO_2$ (50% by weight)
Composition 19*: oxide 12 (50% by weight) and Pd/$SiO_2$ (50% by weight)
Composition 20*: oxide 13 (50% by weight) and Pd/$SiO_2$ (50% by weight)
Composition 21*: oxide 1 (33.3% by weight) and Pd/$SiO_2$ (67.7% by weight); this composition corresponds to the catalyst composition used in table 3, last entry, in EP-A-2772478
Composition 22*: oxide 1 (9% by weight) and Pd/$SiO_2$ (91% by weight); this composition comprises the same constituents as the catalyst compositions used in table 3, last entry, and table 4, fourth and fifth entry, in EP-A-2772478
not according to the invention
Compositions 1, 21 and 22 comprise no mixed oxide for the purposes of the invention; they are physical mixtures of zirconium dioxide and silicon dioxide ($SiO_2$ as support).

Example E

Pd Supported on Mixed Oxide (Catalyst System III)

75 g of oxide mouldings according to Example C were weighed in a polybag. In parallel, 3.75 g of a 10% strength Pd(II) nitrate solution were weighed and diluted to 45 ml by adding water. The diluted solution was poured onto the mouldings in the polybag, and the bag was always shaken again until the liquid was distributed homogeneously on the mouldings. The impregnated mouldings were dried at 110° C. for 2.5 hours, and then calcined for 10 hours in a reducing atmosphere (0.4% by volume hydrogen in the nitrogen) at 200° C. The weight fraction of Pd in the catalyst, based on the total weight of the mixed oxide, was 0.5%.

Catalyst Compositions:
Composition 23*: Oxide 1 supported with 0.5% by weight Pd
Composition 24*: Oxide 1 supported with 0.5% by weight Pd (95% by weight), after the impregnation and calcination mixed with $SiO_2$ Aerosil® 200V (5% by weight). Here, a physical mixture of $ZrO_2$ and $SiO_2$ is present, not a mixed oxide.
Composition 25: Oxide 3 with 0.5% by weight Pd
not according to the invention Catalyst Test Gas chromatography (GC): Gas chromatographic investigations were carried out using a GC-2010 (Shimadzu) chromatograph, fitted with autosampler, flame ionization detector (FID), and GC capillary column Supelcowax® (60 m×0.32 mm×0.25 μm, Supelco). Measurements were carried out in the split mode (Split rate 1:66) with helium as carrier gas (flow rate 0.89 ml/min, linear carrier gas rate 17.9 cm/sec). Temperature program for GC oven: Start temperature 150° C.; heat to 180° C. at 5° C./min, hold for 10 min; heat to 200° C. at 5° C./min, hold for 10 min. Detector and injector temperatures were 340 and 220° C.

Example 1

Comparison of Different Oxides (Catalyst System II)

The reaction was carried out in a 500 ml round-bottomed flask with mechanical stirring. The heating of the reactor was carried out with an electric aluminum heating block and the internal temperature was controlled using a thermosensor. The flask was filled with 50 ml of 1,2-cyclododecane epoxide, 20 g of catalyst compositions from Example D. The catalyst bed lay at the bottom of the flask and the liquid reaction mixture was stirred above the bed. The flask was then rendered inert with nitrogen and heated to an internal temperature of 215° C. The temperature was held for 1.5 hours.

TABLE 2

Composition (area %, GC) of the reaction mixture (after 1.5 h)

| Catalyst composition | Conversion (%) | Selectivity (%) | | | | |
|---|---|---|---|---|---|---|
| | | CDAN | CDEN | CDON + CDENON | CDOL | CDENOL |
| 1* (physical mixture) | 28 | 0 | 0 | 74 | 6 | 18 |
| 2 (ZrO$_2$—SiO$_2$ 95/5) | 64 | 0.6 | 0 | 79 | 6 | 14 |
| 4 (ZrO$_2$—SiO$_2$ 99/1) | 55 | 0 | 0 | 90 | 5 | 5 |
| 5 (ZrO$_2$—SiO$_2$ 97/3) | 71 | 0 | 0.6 | 81 | 9 | 10 |
| 3 (ZrO$_2$—SiO$_2$ 95/5) | 97 | 0.4 | 3 | 79 | 6 | 11 |
| 6 (ZrO$_2$—SiO$_2$ 95/5) | 80 | 0.1 | 1.5 | 79 | 7 | 10 |
| 7 (ZrO$_2$—SiO$_2$ 90/10) | 97 | 0.1 | 5 | 69 | 9 | 13 |
| 8* (ZrO$_2$—SiO$_2$ 85/15, BET > 200) | 95 | 0 | 10 | 66 | 6 | 17 |
| 9* (Organo-Si source) | 77 | 0 | 2 | 16 | 1 | 72 |
| 16* (TiO$_2$—SiO$_2$ 95/5) | 51 | 1 | 1 | 3 | 0.5 | 60 |
| 17* (TiO$_2$—SiO$_2$ 95/5) | 60 | 0.9 | 2 | 7 | 0.7 | 63 |
| 18* (SiO$_2$) | <1 | Not relevant | | | | |
| 19* (ZrO$_2$—SiO$_2$ 15/85) | 86 | 0.3 | 9 | 70 | 9 | 11 |
| 20* (ZrO$_2$—SiO$_2$ 15/85) | >99 | <1% CDON formed, (see table 4) | | | | |

*not according to the invention

Table 2 shows the selectivities for CDO and CDENON in summary since these are technically relevant. The background is that CDENON is usually reacted by the addition of hydrogen in CDON. In this regard, CDENON is not a byproduct. Nevertheless, for the sake of completeness, CDON and CDENON are differentiated in table 3 below.

TABLE 3

Composition (area %, GC) of the reaction mixture (after 1.5 h) according to table 2; division of the mixture CDON + CDENON

| Catalyst composition | Conversion (%) | Selectivity (%) | | |
|---|---|---|---|---|
| | | CDON | CDENON | CDON + CDENON |
| 1* (physical mixture) | 28 | 68 | 6 | 74 |
| 2 (ZrO$_2$—SiO$_2$ 95/5) | 64 | 72 | 7 | 79 |
| 4 (ZrO$_2$—SiO$_2$ 99/1) | 55 | 84 | 6 | 90 |
| 5 (ZrO$_2$—SiO$_2$ 97/3) | 71 | 74 | 7 | 81 |
| 3 (ZrO$_2$—SiO$_2$ 95/5) | 97 | 69 | 10 | 79 |
| 6 (ZrO$_2$—SiO$_2$ 95/5) | 80 | 69 | 10 | 79 |
| 7 (ZrO$_2$—SiO$_2$ 90/10) | 86 | 54 | 15 | 69 |
| 8* (ZrO$_2$—SiO$_2$ 85/15, BET >200) | 95 | 52 | 14 | 66 |
| 9* (Organo-Si source) | 77 | 12 | 4 | 16 |
| 16* (TiO$_2$—SiO$_2$ 95/5) | 51 | 0 | 3 | 3 |
| 17* (TiO$_2$—SiO$_2$ 95/5) | 60 | 0 | 7 | 7 |
| 18* (SiO$_2$) | <1 | Not relevant | | |
| 19* (ZrO$_2$—SiO$_2$ 15/85) | 86 | 53 | 17 | 70 |
| 20* (ZrO$_2$—SiO$_2$ 15/85) | >99 | <1% CDON formed (see table 4) | | |

*not according to the invention

With the same reaction time, the conversion with composition 1 was considerably lower than with compositions 2 to 7. It was found that the mixed oxides ZrO$_2$—SiO$_2$ have a much higher catalytic activity than pure ZrO$_2$ from the related art for a similar selectivity to the ketone. The activity increased with the fraction of SiO$_2$ in the mixed oxide.

With composition 8, 10% of the by-product CDEN were obtained, meaning that this catalyst cannot be used cost-effectively on account of the low selectivity. An SiO$_2$ fraction of >15% by weight in the mixed oxide and a BET surface area >200 m$^2$/g are not preferred for this reason.

Compositions 9 (organosilicon source) and 16 and 17 (chemical mixture of $TiO_2$ and $SiO_2$) exhibit a very low selectivity to CDON.

Composition 18 has no catalytic activity. This experiment confirms that $ZrO_2$ in the catalyst system forms an obligatory necessary constituent.

Composition 19 (zirconium dioxide-doped silicon oxides) exhibits relatively high conversions and high selectivities. However, the data presented in tables 2 and 3 do not take into consideration the formation of high boilers (oligomers and polymers) which are formed during the reaction. The values for the high boilers are taken into consideration in table 4 below.

TABLE 4

Composition (% by weight, calculated with GC factors) of some reaction mixtures after 5 h taking into consideration the high boilers

| Catalyst composition | CDAN + CDEN | Epoxide | CDON | CDENON | CDOL | CDENOL | High boilers (oligomers/ polymers) |
| --- | --- | --- | --- | --- | --- | --- | --- |
| 1* (physical mixture) | 0.3 | 42 | 51 | 3 | 2.6 | 1.7 | 0.3 |
| 3 ($ZrO_2$—$SiO_2$ 95/5) | 2.7 | 0 | 79 | 9 | 5 | 1.4 | 2.6 |
| 19* ($ZrO_2$—$SiO_2$ 15/85) | 9 | 0 | 54 | 12 | 5 | 2.4 | 17 |
| 20* ($ZrO_2$—$SiO_2$ 15/85) | 1 | 0.4 | 0.5 | 9 | 0.25 | 4 | 85 |

*not according to the invention

With compositions 19 and 20, in each case zirconium-doped silicon dioxide, fractions of 17% and 85%, respectively, of high boilers are obtained. The composition according to the invention comprising the mixed oxide, by contrast, has only 2.6% high boilers as byproduct. Consequently, a zirconium dioxide-doped or coated silicon dioxide is not suitable as catalyst system.

Example 2

Comparison of Different Oxides (Catalyst System II)—Progress with Time

The aforementioned reaction in example 1 was continued for compositions 1 and 3 up to a reaction time of 5 h. Samples were taken regularly and the conversion of the starting material 1,2-cyclododecane epoxide was determined. Moreover, a further experiment with 30 g of composition 21 was carried out.

TABLE 5

Conversion of the starting material 1,2-cyclodo decane epoxide over a period of 5 h (area %, GC)

| Catalyst composition | Symbol in FIG. 1 | Conversion of starting material | | | | |
| --- | --- | --- | --- | --- | --- | --- |
| | | 0 h | 0.5 h | 1.5 h | 3.0 h | 5.0 h |
| 1* (physical mixture) | Diamond | 0% | 5% | 28% | 46% | 58% |
| 3 ($ZrO_2$—$SiO_2$ 95/5) | Square | 0% | 67% | 97% | 100% | 100% |
| 21* (physical mixture) | Triangle | 0% | 40% | 80% | 94% | 100% |

*not according to the invention

Composition 3 according to the invention leads, after just 1.5 h, to a virtually complete conversion of the starting material used, which reaches 100% after 3 h. Mixture 1 does not achieve this value even after a reaction time of 5 h. Although mixture 21 of the related art (EP-A-2772478, table 3, last entry) likewise exhibits a complete conversion, this is present only after a significantly longer reaction time and is achieved with a larger amount of catalyst composition.

The progress of the composition is shown graphically in Figure 1. Here, the conversion U of 1,2-cyclododecane epoxide (in %) was plotted against the reaction time t in hours.

Example 3

Precious Metal Supported on the Mixed Oxide (Catalyst System III)

The reaction was carried out in a 500 ml round-bottomed flask with mechanical stirring. The heating of the reactor was carried out with an electric aluminum heating block and the internal temperature was controlled using a thermosensor. The flask was filled with 50 ml of 1,2-cyclododecane epoxide and the catalyst composition (Example E). The catalyst bed lay at the bottom of the flask and the liquid reaction mixture was stirred above the bed. The flask was then rendered inert with nitrogen and heated to an internal temperature of 215° C. The temperature was held for 1.5 hours.

TABLE 6

Composition (area %, GC) of the reaction mixture (after 1.5 h)

| Catalyst composition | Amount (g) | Conversion (%) | Selectivity (%) | | | | |
|---|---|---|---|---|---|---|---|
| | | | CDAN | CDEN | CDON | CDOL | CDENOL |
| 23* ($ZrO_2$) | 10 | 35 | 0 | 0 | 94 | 4 | 0 |
| 25 ($ZrO_2$—$SiO_2$ 95/5) | 10 | 98 | 0.3 | 1.1 | 79 | 8 | 3 |
| 23* ($ZrO_2$) | 20 | 80 | 1 | 0 | 96 | 3 | 0 |
| 24* (physical mixture) | 20 | 69 | 1 | 0 | 97 | 2 | 0 |
| 25 ($ZrO_2$—$SiO_2$ 95/5) | 20 | >99 | 0.5 | 1.4 | 87 | 5 | 2 |

*not according to the invention

Example 3 has demonstrated that $ZrO_2$-$SiO_2$ mixed oxides of catalyst system III have a catalytic activity. This turned out to be considerably higher for the mixed oxide (composition 25) than for catalysts without $SiO_2$ (composition 23) or catalysts comprising a physical mixture of $ZrO_2$ and $SiO_2$ (composition 24).

Example 4

Optimized Reaction Conditions (Catalyst System II)

The reaction was carried out in a 500 ml round-bottomed flask with mechanical stirring. The heating of the reactor was carried out with an electric aluminum heating block and the internal temperature was controlled using a thermosensor. The flask was filled with 50 ml of 1,2-cyclododecane epoxide and 13 g of the catalyst composition. The catalyst bed lay at the bottom of the flask and the liquid reaction mixture was stirred above the bed. The flask was then rendered inert with nitrogen and heated to an internal temperature of 215° C. The temperature was held for 6 hours.

The weight ratio of $ZrO_2$ to $SiO_2$ was 95:5 for all three catalyst compositions. Similarly, the weight ratio of oxide to Pd on an inert support was identical (23:67). The oxides were prepared either from zirconium hydroxide or from zirconium hydroxide and a compound B.

A second zirconium compound B, in addition to the zirconium hydroxide A, was added in the preparation of the mixed oxides 10 and 11. Composition 13 was prepared with zirconium hydroxide A as single Zr source. The catalyst compositions are thus suitable for the rearrangement of the epoxide to the ketone irrespective of the composition of the zirconium compound.

Analogously to table 7, the fractions of CDON and CDENON are listed individually in table 8.

TABLE 8

Composition (area %, GC) of the reaction mixture (after 1.5 h) according to table 7; division of the mixture CDON + CDENON

| Catalyst composition | Conversion (%) | Selectivity (%) | | |
|---|---|---|---|---|
| | | CDON | CDENON | CDON + CDENON |
| 10 (ammonium zirconium carbonate) | 98 | 79 | 8 | 87 |
| 11 (zirconyl nitrate) | 67 | 79 | 9 | 88 |
| 13 (no compound B) | 98 | 84 | 7 | 91 |

TABLE 7

Composition (area %, GC) of the reaction mixture (after 6 h)

| Catalyst composition | Conversion (%) | Selectivity (%) | | | | |
|---|---|---|---|---|---|---|
| | | CDAN | CDEN | CDON + CDENON | CDOL | CDENOL |
| 10 (Ammonium zirconium carbonate) | 98 | 1 | 0.4 | 87 | 5 | 4 |
| 11 (Zirconyl nitrate) | 67 | 0.1 | 1.3 | 88 | 6 | 4 |
| 13 (no compound B) | 98 | 0.1 | 1.2 | 91 | 4 | 1.3 |

Example 5

Optimized Reaction Conditions (Catalyst System II)

The reaction was carried out in a 500 ml round-bottomed flask with mechanical stirring. The heating of the reactor was carried out with an electric aluminum heating block and the internal temperature was controlled using a thermosensor. The flask was filled with 50 ml of 1,2-cyclododecane epoxide, and 10 g of 0.5% by weight palladium on silicon dioxide as moulding and the mixed oxide of the catalyst system (moulding). The catalyst bed lay at the bottom of the flask and the liquid reaction mixture was stirred above the bed. The flask was then rendered inert with nitrogen and heated to an internal temperature of 180 to 215° C. The temperature was held over the stated time.

TABLE 9

Composition (area %, GC) of the reaction mixture

| Catalyst composition | Mixed oxide | Temp (° C.) | Time (h) | Conversion (%) | Selectivity (%) | | | |
|---|---|---|---|---|---|---|---|---|
| | | | | | CDAN | CDEN | CDON + CDENON | CDOL |
| 1* | 10 g oxide 1 | 215 | 5 | 58 | 0 | 0.2 | 92 | 4 |
| 22* | 1 g oxide 1 | 215 | 5 | 13 | 0 | 0 | 95 | 4 |
| 12 | 1 g oxide 3 | 215 | 5 | 50 | 0.4 | 1 | 92 | 3 |
| 1* | 10 g oxide 1 | 215 | 24 | 98 | 0 | 0 | 97 | 2 |
| 22* | 1 g oxide 1 | 215 | 24 | 38 | 0 | 0 | 96 | 3 |
| 12 | 1 g oxide 3 | 215 | 24 | 98 | 0 | 1.5 | 94 | 4 |
| 13 | 3 g oxide 3 | 200 | 24 | 99 | 0.2 | 0.5 | 95 | 3 |
| 1* | 10 g oxide 1 | 180 | 24 | 19 | 0 | 0 | 94 | 3 |
| 3 | 10 g oxide 3 | 180 | 24 | >99 | 0 | 0.7 | 93 | 5 |

*not according to the invention

TABLE 10

Composition (area %, GC) of the reaction mixture according to table 9; division of the mixture CDON + CDENON

| Catalyst composition | Mixed oxide | Temp (° C.) | Time (h) | Conversion (%) | Selectivity (%) | | |
|---|---|---|---|---|---|---|---|
| | | | | | CDON | CDENON | CDON + CDENON |
| 1* | 10 g oxide 1 | 215 | 5 | 58 | 87 | 5 | 92 |
| 22* | 1 g oxide 1 | 215 | 5 | 13 | 94 | 1 | 95 |
| 12 | 1 g oxide 3 | 215 | 5 | 50 | 75 | 17 | 92 |
| 1* | 10 g oxide 1 | 215 | 24 | 98 | 95 | 2 | 97 |
| 22* | 1 g oxide 1 | 215 | 24 | 38 | 95 | 1 | 96 |
| 12 | 1 g oxide 3 | 215 | 24 | 98 | 87 | 7 | 94 |
| 13 | 3 g oxide 3 | 200 | 24 | 99 | 90 | 5 | 95 |
| 1* | 10 g oxide 1 | 180 | 24 | 19 | 92 | 2 | 94 |
| 3 | 10 g oxide 3 | 180 | 24 | >99 | 86 | 7 | 93 |

*not according to the invention

A comparison of composition 12 according to the invention (ZrO2-SiO2 mixed oxide) with compositions 1 and 22 not according to the invention (related art) over a reaction time of 5 h at 215° C. demonstrates that less than 1/10 of ZrO2 is required for the same catalytic activity. With the same amount of zirconium dioxide, composition 12 according to the invention exhibits a much higher catalytic activity than composition 22 (related art).

The 24-hour experiment demonstrates that for a similarly high conversion with a simultaneously similarly high selectivity, compared to composition 1, less catalyst (compositions 12, 13) or a lower temperature are required (compositions 13, 3).

Example 6

Reaction of Epoxide

The reaction was carried out in a 500 ml round-bottomed flask with mechanical stirring. The heating of the reactor was carried out with an electric aluminum heating block and the internal temperature was controlled using a thermosensor. The flask was filled with 50 ml of 1,2-cyclododecane epoxide, 10 g of 0.5% by weight of palladium on silicon dioxide as moulding and 5 g of oxide 3 (corresponds to 15 g of composition 14). The catalyst bed lay at the bottom of the flask and the liquid reaction mixture was stirred above the bed. A mixture of hydrogen and nitrogen was introduced during the reaction (1 bar with 90% by volume H2 and 10% by volume N2). The flask was then heated to an internal temperature of 215° C. The temperature was held for 5 hours. At the end of the experiment, a mixture of CDON (87.2%), CDOL (8.4%), CDAN (2%) and CDENOL (1%) was obtained.

Example 7

Fixed-Bed Method

The reaction was carried out in a fixed-bed arrangement. The arrangement consisted of two fixed-bed reactors in series (approx. 200 ml per reactor) and a steel storage container (1 l). The lower fixed-bed reactor was filled with 50 g of oxide 6 and the upper fixed-bed reactor was filled with 200 g of 0.5% $Pd/SiO_2$ from Example D. This composition corresponds to 250 g of catalyst composition 15. The container was filled with 1500 g of 1,2-cyclododecane epoxide. The liquid was pumped in a cycle from the storage container from bottom to top through the catalyst bed back to the storage container using a circulating pump (10 l/h). The reactors were heated to 205° C. in the reaction mixture using electrical heating. The reaction mixture was passed through the fixed-bed reactors and the container with nitrogen. After a reaction of 30 h, a conversion of 78% with a selectivity of approx. 93% CDON was achieved.

The reaction can be carried out with the catalyst systems according to the invention in fixed-bed reactors. This experiment also shows that both components of catalyst system II ($ZrO_2$—$SiO_2$ mixed oxide as moulding and $Pd/SiO_2$ moulding) can be used in spatially separate reactors without an adverse effect on the activity and selectivity.

European patent application EP14187482 filed Oct. 2, 2014, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:
1. A catalyst composition, comprising:
   at least one precious metal; and
   at least one mixed oxide;
   wherein the mixed oxide comprises zirconium dioxide and silicon dioxide;
   wherein the precious metal is supported and the support is not entirely made of the mixed oxide; and
   wherein a mass ratio of zirconium dioxide to silicon dioxide in the mixed oxide is 86:14 to 99.9:0.1.
2. The catalyst composition according to claim 1, wherein the support does not comprise the mixed oxide.
3. The catalyst composition according to claim 1, wherein the support of the precious metal is selected from the group consisting of silicon dioxide, aluminum oxide and mixtures thereof.
4. The catalyst composition according to claim 1, wherein the precious metal is selected from the group consisting of ruthenium, rhodium, palladium, osmium, iridium, platinum and mixtures thereof.
5. The catalyst composition according to claim 1, wherein the precious metal is palladium.
6. A process for producing a catalyst composition according to claim 1, comprising:
   a) preparing a mouldable mass which at least comprises
      i. a zirconium compound,
      ii. silicon dioxide as solid, and
      iii. water, and
   b) calcining the mouldable mass at a temperature of from 300 to 500° C. to prepare the mixed oxide.
7. The process according to claim 6, wherein the precious metal is impregnated on an inert support to produce the catalyst system.
8. The process according to claim 6,
   wherein the catalyst composition comprises at least one precious metal and at least one mixed oxide,
   wherein the mixed oxide comprises zirconium dioxide and silicon dioxide,
   wherein the specific surface area of the mixed oxide, measured according to BET methods, is 5-155 $m^2/g$,
   wherein the precious metal is supported on the mixed oxide,

TABLE 11

| Composition (area %, GC) of the reaction mixture | | | | | | | |
|---|---|---|---|---|---|---|---|
| Temp | Time | Conversion | Selectivity (%) | | | | |
| (° C.) | (h) | (%) | CDAN | CDEN | CDON | CDENON | CDOL | CDENOL |
| 205 | 30 | 78 | 0.4 | 1 | 93 | 0.9 | 4 | 0.4 | wherein the mixed oxide has a monomodal pore radius distribution, and
wherein the mass ratio of zirconium dioxide to silicon dioxide in the mixed oxide is 86:14 to 99.9:0.1, wherein,
a) a mouldable mass is prepared which at least comprises
  i. a zirconium compound,
  ii. silicon dioxide as solid having a particle size $d_{50}$, as measured by laser diffraction, of at least 100 nm,
  iii. water, and
b) the mouldable mass is calcined at a temperature of from 300 to 500° C. to prepare the mixed oxide.

9. The process according to claim 8, wherein the precious metal is impregnated on the mixed oxide as support.

10. The process according to claim 6, wherein the particle size $d_{50}$, as measured by laser diffraction, of the silicon dioxide is 100 nm to 500 μm.

11. The process according to claim 6, wherein the zirconium compound is selected from the group consisting of zirconium dioxide, zirconium hydroxide, zirconium acetate, zirconium nitrate, zirconium oxychloride, ammonium zirconium carbonate and mixtures thereof.

12. The process according to claim 6, wherein the zirconium compound is selected from the group consisting of zirconium dioxide, zirconium hydroxide and mixtures thereof.

13. The process according to claim 6, wherein the zirconium compound is a mixture of A and B, wherein A is selected from the group consisting of zirconium dioxide, zirconium hydroxide and mixtures thereof; and B is selected from the group consisting of zirconium acetate, zirconium nitrate, zirconium oxychloride, ammonium zirconium carbonate and mixtures thereof.

14. The process according to one of claim 6, wherein the mouldable mass is reshaped to give mouldings prior to the calcination.

15. A process for producing a ketone, comprising:
reacting a compound containing at least one epoxide group in the presence of a catalyst composition;
wherein the catalyst composition comprises at least one precious metal and at least one mixed oxide, wherein the mixed oxide comprises zirconium dioxide and silicon dioxide, wherein the precious metal is supported on a support and wherein a mass ratio of zirconium dioxide to silicon dioxide in the mixed oxide is 86:14 to 99.9:0.1, and wherein the support is the mixed oxide or the support does not consist of the mixed oxide.

16. The process according to claim 15, wherein the ketone is cyclododecanone.

17. A process for the synthesis of a lactam, comprising:
producing a ketone according to claim 15 and reacting said ketone to produce said lactam.

* * * * *